United States Patent [19]

Reinink et al.

[11] 3,993,703

[45] Nov. 23, 1976

[54] PREPARATION OF 2-HYDROCARBYLGLYCEROLS

[75] Inventors: Arend Reinink; Jennigje Grendelman, both of Amsterdam, Netherlands

[73] Assignee: Shell Oil Company, Houston, Tex.

[22] Filed: Aug. 21, 1975

[21] Appl. No.: 606,674

[30] Foreign Application Priority Data

Sept. 5, 1974 United Kingdom............... 38836/74

[52] U.S. Cl.......................... 260/635 P; 260/617 R; 260/618 R; 260/636
[51] Int. Cl.².......................................... C07C 29/00
[58] Field of Search ........................ 260/635 P, 636

[56] References Cited

UNITED STATES PATENTS 2,761,881  9/1956  Rosin............................... 260/635 P

OTHER PUBLICATIONS

Monick, "Alcohols," (1968), pp. 366–367.
Houben–Weyl, "Methoden der Organischen Chemie," 4th ed., vol. VII, part 1 (1954), pp. 363, 374, 375.

*Primary Examiner*—Joseph E. Evans

[57] ABSTRACT

Manufacture of 2-hydrocarbylglycerols by contacting a 2-haloalkanal with a secondary carbon atom in the 2-position, with formaldehyde in the presence of an aqueous solution containing an alkaline-reacting compound at a concentration of at least 0.5 gram-equivalent per liter of water.

10 Claims, No Drawings

PREPARATION OF 2-HYDROCARBYLGLYCEROLS

BACKGROUND OF THE INVENTION

1. Field of the Invention

The invention relates to a process for the preparation of a 2-hydrocarbylglycerol, a useful intermediate to certain biologically active compounds.

2. Descriptions of the Prior Art

The preparation of 2-methylglycerol, described in J. A. Monick "Alcohols, their Chemistry, Properties and Manufacture" (1968), pp. 366–367 and referred to as "hydrolysis route," consists of withdrawing hydrogen chloride from 1,3-dichloro-2-hydroxy-2-methylpropane with calcium hydroxide with formation of 1-chloro-2,3-epoxy-2-methylpropane, hydrolysis of this epoxide in dilute aqueous sulphuric acid with formation of 2-chloromethyl-1,2-propanediol and reaction of this diol with water in the presence of sodium hydroxide. This route is laborious, involving three steps which must be carried out in three different reaction zones.

In accordance with "Methoden der Organischen Chemie" (Houben-Weyl), fourth edition, volume VII, part 1 (1954), pages 363, 374 and 375, it was found that the hydrolysis of 2-chlorobutanal with an aqueous solution of a carbonate or a hydroxide of an alkali metal involves a very complex reaction and presents great difficulties. Although 2-chlorobutanal was completely converted, the corresponding 2-hydroxybutanal was only obtained in a very low yield, a large number of side products being simultaneously formed.

The present invention offers the possibility of preparing 2-hydrocarbylglycerols in an easy manner.

SUMMARY OF THE INVENTION

The invention may be defined as relating to a process for the preparation of a 2-hydrocarbylglycerol, which comprises reacting a 2-haloalkanal having a secondary carbon atom in the 2-position, with formaldehyde and an alkaline reacting compound, in the presence of an aqueous medium, the concentration of the alkaline reacting compound being at least 0.5 gram-equivalent.

It is surprising that according to the present invention a 2-hydrocarbylglycerol can be obtained from a 2-haloalkanal in a very satisfactory yield; a reaction which inter alia involves the conversion of a halogen atom into a hydroxyl group. The process according to the present invention — hereinafter referred to as "novel process" — is conducted in one step only, one reaction zone being sufficient. Moreover, the 2-hydrocarbylglycerols are usually obtained in a very satisfactory yield.

The carbon atom in the 2-position of the 2-haloalkanal must be secondary, because only then are 2-hydrocarbylglycerols formed. The hydrocarbyl group R may, for example, be an alkyl, cycloalkyl or aryl group. Very good results have been obtained with acyclic 2-haloalkanals, whether straight or branched. Among the 2-haloalkanals the 2-chloroalkanals are preferred. Examples of 2-haloalkanals are 2-chloropropanal, 2-chlorobutanal, 2-chloropentanal, 2-chlorohexanal, 2-chloro-3-methylbutanal, 2-chloro-3,3-dimethylbutanal, 2-chloro-3-methyl-pentanal, 2-chloro-2-cyclohexylethanal, 2-chloro-2-(4'-methyl-cyclohexyl)ethanal, 2-chloro-2-phenylethanal, 2-chloro-2-(4'-methyl-phenyl)ethanal and 2-chloro-2-(1-naphthyl)ethanal and their corresponding 2-bromoalkanals. Very good results have been obtained with 2-chlorobutanal. Mixtures of 2-haloalkanals having a secondary carbon atom in the 2-position may be applied.

The starting 2-haloalkanals are generally easily accessible. For example, 2-chlorobutanal can be prepared by chlorination of butanal in concentrated aqueous hydrochloric acid (Bulletin Soc. Ch.Fr(1953) 222) or in N,N-dimethylformamide in the presence of cupric chloride, as described in J.Org.Chem.28 (1963) 630 for the chlorination of saturated ketones and phenols.

The alkaline reacting compounds used in the novel process are compounds imparting a pH higher than 7 to their aqueous solutions. The alkaline reacting compounds must be applied at a concentration of at least 0.5, preferably of at least 2.5 and more preferably of at least 5 gram-equivalents per liter of water. Solid alkaline reacting compound(s) may also be present, but the novel process is preferably conducted in the absence thereof. The amount of gram-equivalents of solute per liter of solution is the quantity of solute corresponding in a neutralization reaction to one gram-atomic weight of hydrogen. Alkaline reacting compounds having a solubility of less than 0.5 gram-equivalent per liter, measured at the reaction temperature chosen, for example calcium hydroxide, are outside the scope of the novel process, because 2-hydrocarbylglycerols are not or hardly formed under the reaction conditions. Examples of suitable alkaline reacting compounds are carbonates of alkali metals having an atomic number of at least 11 (of sodium, potassium, rubidium and cesium), alkali-metal hydroxides (of lithium, sodium, potassium, rubidium and cesium), alkali-metal cyanides, dialkali-metal hydrogenphosphates, trialkali-metal orthophosphates and quaternary ammonium, phosphonium, arsonium and stibonium bases. Very good results have been obtained with carbonates of alkali metals having an atomic number of at least 11 and alkali-metal hydroxides, particularly sodium hydroxide. Among the alkali-metal carbonates those of sodium and potassium are preferred in view of their relatively low price. Mixtures of alkaline reacting compounds may be used.

The novel process proceeds according to the following general reaction equation when sodium hydroxide is used as the alkaline reacting compound:

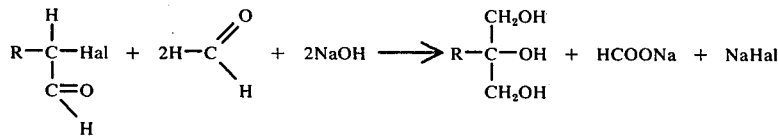

in which R and Hal represent a hydrocarbyl group and a halogen atom, respectively.

The starting molar ratio formaldehyde: 2-haloalkanal, the starting ratio gram-equivalent alkaline reacting compound: 2-haloalkanal and the temperature chosen for the novel process are not critical and may vary within wide limits, also outside the ranges stated below.

The said two ratios preferably will be chosen higher than 2, the stoichiometric ratio according to the above-mentioned reaction equation, and lower than 10, because the yield of 2-hydrocarbylglycerol will generally increase only slightly at molar ratios increasing above 10. The novel process is as a rule conducted at a temperature in the range of from 10° to 200° C, preferably of from 50° C to 100° C and at atmospheric pressure, but super- and sub-atmospheric pressures are within the scope of the invention. Which values of the above-mentioned two ratios and which temperature can best be applied in a specific case can easily be verified experimentally.

The novel process is preferably be conducted by adding an aqueous solution of the alkaline reacting compound to a vigorously stirred mixture of the 2-haloalkanal and an aqueous formaldehyde solution. The reaction is exothermic and the heat of reaction may be withdrawn in any suitable manner, for example by boiling under reflux. When all alkaline reacting compound has been added it will usually be advantageous to stir the reaction mixture vigorously for some time, for example for 2–7 hours, at a temperature of, say, between 90° and 100° C. Then, the 2-hydrocarbylglycerol may be isolated from the reaction mixture in any suitable manner. For example, the mixture is acidified to a pH between 5 and 6, water is distilled off, the distillation residue obtained is extracted with a solvent, for example ethanol, and the extract phase thus obtained is boiled down to obtain the 2-hydrocarbylglycerol.

for some time with vigorous stirring. Subsequently, the mixture was cooled to a temperature of 22° C and 12 N aqueous hydrochloric acid was added to the cooled mixture until the pH was decreased to a value between 5.5 and 6.0. The mixture thus acidified was boiled down in a film evaporator at a pressure of 0.016 bar abs. and a temperature of about 50° C. The residue formed in the film evaporator was mixed with 75 ml 96%w ethanol, the solid compounds not taken up by the ethanol (NaCl and HCOONa) were filtered off and the filtrate was boiled down in a film evaporator at a pressure of 0.016 bar abs. The residue obtained was analysed by gas-liquid chromatography. The Table provides data on each individual experiment. The alkaline reacting compound used and the amounts of formaldehyde and of the alkaline reacting compound are stated in the second, third and fourth column, respectively, from the left. The concentration of the alkaline reacting compound in the aqueous solution added is stated in the fifth column and the concentration of the alkaline reacting compound in the water present in the reaction mixture — which also includes the water originating from the formaldehyde solution —, stated in the sixth column, has been calculated from the data given. The seventh column states the reaction time after addition of the alkaline reacting compound and the yield of 2-ethylglycerol, calculated on starting 2-chlorobutanal, is presented in the first column from the right. In all experiments the addition of the aqueous solution of the alkaline reacting compound caused generation of heat, which was withdrawn using the reflux condenser.

TABLE

| Exp. No. | Alkaline reacting compound | Amounts in mol formaldehyde | alkaline reacting compound | Concentration of alkaline reacting compound, | | Reaction time after addition of alkaline reacting compound | Yield % mol. |
|---|---|---|---|---|---|---|---|
| | | | | as added %w | in reaction mixture g-equiv. l water | | |
| 1 | $K_2CO_3$ | 0.6 | 0.25 | 50 | 7.5 | 4.5 | 71 |
| 2 | $Na_2CO_3$ | 0.4 | 0.25 | 30 | 6.0 | 6 | 66 |
| 3 | NaOH | 0.8 | 0.50 | 50 | 8.0 | 3 | 64 |
| 4 | NaOH | 0.8 | 0.50 | 25 | 4.9 | 3 | 33 |
| 5 | NaOH | 0.4 | 0.50 | 50 | 12.1 | 3 | 60 |
| 6 | $Ca(OH)_2$ | 0.4 | 0.25 | —**) | 0.01 | 3 | 0 |
| 7 | KOH | 0.4 | 0.50*) | 50 | 10.1 | 3 | 32 |
| 8 | $K_2CO_3$ | 2.5 | 1.25 | 50 | 7.5 | 4.5 | 75 |

*)actually 0.45 mol, the KOH having a purity of 90%.
**)the $Ca(OH)_2$ was added with 43 ml water.

Derivatives of 2-alkylglycerols are biologically active, possessing in particular herbicidal, plant-growth-regulating and fungicidal properties, as disclosed in British Pat. specification 1,293,546.

The invention is further illustrated by means of the following Example which is for the purpose of illustration.

EXAMPLE

Six experiments were carried out as follows. A mixture of 0.1 mol 2-chlorobutanal and a 36%w aqueous formaldehyde solution was heated up at atmospheric pressure with vigorous stirring until refluxing started. The boiling mixture had a temperature of 95° C. Throughout the experiments nitrogen was passed through the mixture. Then, an aqueous solution of an alkaline reacting compound was gradually added to the mixture over a period of 10 min. When the solution had been added the mixture was allowed to react at 95° C

What we claim is:

1. A process for the preparation of a 2-alkylglycerol which comprises reacting at a temperature in the range of from 10° C to 200° C a 2-haloalkanal having a secondary carbon atom in the 2-position with formaldehyde and an alkaline reacting compound in the presence of an aqueous medium, the concentration of the alkaline reacting compound being at least 0.5 gram-equivalent.

2. A process as claimed in claim 1, wherein the 2-haloalkanal is a 2-chloroalkanal.

3. A process as claimed in claim 2, wherein the 2-chloroalkanal is 2-chlorobutanal.

4. A process as claimed in claim 1, wherein the alkaline reacting compound is used in a concentration of at least 2.5 gram-equivalent.

5. A process as claimed in claim 1, wherein the alkaline reacting compound is sodium carbonate, potassium carbonate or sodium hydroxide.

6. A process as claimed in claim 1, wherein the starting molar ratio formaldehyde: 2-haloalkanal is between 2 and 10.

7. A process as claimed in claim 1, wherein the starting ratio gram-equivalent alkaline reacting compound: 2-haloalkanal is between 2 and 10.

8. A process as claimed in claim 1, wherein the reaction is effected at a temperature in the range of from 50° to 100° C.

9. A process as claimed in claim 1, wherein an aqueous solution of the alkaline reacting compound is added to a vigorously stirred mixture of a 2-haloalkanal and an aqueous formaldehyde solution.

10. A process as claimed in claim 1 wherein the alkaline reacting compound is used in a concentration of at least 5 gram-equivalent.

* * * * *